United States Patent
Piantoni et al.

(10) Patent No.: US 10,842,686 B2
(45) Date of Patent: Nov. 24, 2020

(54) UNIT FOR FEEDING LATERAL FLAPS OF A HYGIENE ABSORBENT ARTICLE AND METHOD FOR THE FORMAT CHANGE OF THE FEEDING UNIT

(71) Applicant: GDM S.p.A., Bologna (IT)

(72) Inventors: Matteo Piantoni, Albino (IT); Valerio Soli, Bologna (IT); Federico Tordini, Pedrengo (IT); Marco Rosani, Vailate (IT); Mauro Pietralunga, Crema (IT)

(73) Assignee: GDM S.p.A., Bologna (IT)

( * ) Notice: Subject to any disclaimer, the term of this patent is extended or adjusted under 35 U.S.C. 154(b) by 119 days.

(21) Appl. No.: 16/074,908

(22) PCT Filed: Feb. 9, 2017

(86) PCT No.: PCT/IB2017/050695
§ 371 (c)(1),
(2) Date: Aug. 2, 2018

(87) PCT Pub. No.: WO2017/137909
PCT Pub. Date: Aug. 17, 2017

(65) Prior Publication Data
US 2019/0060133 A1 Feb. 28, 2019

(30) Foreign Application Priority Data
Feb. 9, 2016 (IT) .................. 102016000012998

(51) Int. Cl.
*A61F 13/15* (2006.01)
(52) U.S. Cl.
CPC .. *A61F 13/15756* (2013.01); *A61F 13/15723* (2013.01); *A61F 13/15764* (2013.01)
(58) Field of Classification Search
CPC .......... A61F 13/15756; A61F 13/15723; A61F 13/15764
See application file for complete search history.

(56) References Cited

U.S. PATENT DOCUMENTS 4,726,876 A * 2/1988 Tomsovic, Jr. ... A61F 13/15601
156/552
4,767,487 A * 8/1988 Tomsovic, Jr. ... A61F 13/15601
156/256
(Continued)

FOREIGN PATENT DOCUMENTS

CN 104168867 A 11/2014
CN 104812350 A 7/2015
(Continued)

OTHER PUBLICATIONS

International Application No. PCT/IB2017/050695, International Search Report and Written Opinion, dated May 11, 2017.
(Continued)

*Primary Examiner* — Nathaniel C Chukwurah
*Assistant Examiner* — Lucas E. A. Palmer
(74) *Attorney, Agent, or Firm* — Marshall, Gerstein & Borun LLP

(57) ABSTRACT

The unit for feeding lateral flaps of a hygiene absorbent article having: an input conveyor of a first continuous strip; a cutting assembly provided with a receiving drum, of the first suction-pick up heads that hold the lateral flaps and which are mounted to as to be radially movable on the receiving drum, and at least one blade which cyclically cuts the first strip crosswise; a spacer assembly having a pair of spacer drums provided with second suction-pick up heads that receive the lateral flaps of the receiving drum; and an actuator system, which cyclically moves each first suction-pick up head radially between a radial pick-up position and a radial release position, in the area of an output station.

12 Claims, 3 Drawing Sheets

(56) References Cited

U.S. PATENT DOCUMENTS

| | | | |
|---|---|---|---|
| 6,848,566 B2* | 2/2005 | Harnish | B65G 29/00 198/459.8 |
| 8,016,972 B2* | 9/2011 | Andrews | A61F 13/15756 156/265 |
| 8,820,513 B2* | 9/2014 | Papsdorf | A61F 13/15764 198/478.1 |
| 9,944,487 B2* | 4/2018 | McCabe | A61F 13/15723 |
| 2010/0192739 A1* | 8/2010 | Piantoni | B65H 39/14 83/26 |
| 2012/0152447 A1* | 6/2012 | Schneider | A61F 13/15747 156/227 |
| 2012/0190523 A1* | 7/2012 | Pastrello | A61F 13/15756 493/343 |
| 2013/0239764 A1* | 9/2013 | McCabe | A61F 13/15723 83/100 |
| 2014/0249010 A1* | 9/2014 | Piantoni | A61F 13/15756 493/343 |
| 2015/0024919 A1* | 1/2015 | Shimada | A61F 13/5622 493/344 |
| 2015/0297416 A1* | 10/2015 | Piantoni | A61F 13/15756 156/517 |
| 2017/0252223 A1* | 9/2017 | Piantoni | A61F 13/15756 |
| 2018/0104112 A1* | 4/2018 | Piantoni | A61F 13/15764 |

FOREIGN PATENT DOCUMENTS

| | | |
|---|---|---|
| GB | 2495101 A | 4/2013 |
| JP | 2015514050 A | 5/2015 |
| WO | WO-2008/001209 A2 | 1/2008 |
| WO | WO-2008/037281 A1 | 4/2008 |
| WO | WO-2013/035067 A1 | 3/2013 |
| WO | WO-2013/158599 A1 | 10/2013 |
| WO | WO-2014/087293 A1 | 6/2014 |

OTHER PUBLICATIONS

International Application No. PCT/IB2017/050695, International Preliminary Report on Patentability, dated Jan. 25, 2018.

Office Action, Chinese Patent Application No. 201780010139.6, dated Aug. 12, 2020.

* cited by examiner

UNIT FOR FEEDING LATERAL FLAPS OF A HYGIENE ABSORBENT ARTICLE AND METHOD FOR THE FORMAT CHANGE OF THE FEEDING UNIT

This is the U.S. national phase of International Application No. PCT/IB2017/050695, filed Feb. 9, 2017, which claims the benefit of Italian Patent Application No. 102016000012998, filed on Feb. 9, 2016.

TECHNICAL FIELD

The present invention relates to a unit for feeding lateral flaps of a hygiene absorbent article and a method for the format change of the feeding unit.

PRIOR ART

According to what is known the hygiene absorbent articles, such as diapers, are obtained by superimposing a sheet of impermeable material to a sheet of permeable material (non-woven fabric) and by interposing a padding formed by an absorbent pad between said sheets.

Both in the case of baby diapers, and of adult diapers, it is usual to provide accessory components, such as lateral closing flaps of the diaper around the waist line of the users. Generally, the lateral closing flaps are applied along given sections of a continuous strip of absorbent material, said sections are then divided into the single diapers.

The cutting machining of the lateral flaps and the subsequent application of the same on the continuous strip of absorbent material takes place by means of a unit for feeding the lateral flaps. The unit for feeding lateral flaps of a known type, as described for example in documents WO2014087293 and WO2013035067, comprise a conveyor for feeding a continuous strip, a cutting assembly of the strip into single lateral flaps, a spacer assembly that spaces the lateral flaps of a same pair of lateral flaps one from the other, and an assembly for forming and applying pairs of lateral flaps to the continuous strip of absorbent material.

It is clear that by changing the type of absorbent article to be obtained, the size and the format of the lateral flaps also change. It follows that, by changing the size and/or the format of the lateral flaps, it is necessary to replace entire assemblies of the unit for feeding the lateral flaps with other assemblies suitable to operate according to the new format of the absorbent article and of the lateral flaps to be applied. In other words, with the known units for feeding lateral flaps, during the format change the replacement of the cutting assembly with another cutting assembly having drums of different diameter is required; therefore, it is necessary to replace the spacer assembly with another spacer assembly having a diameter adapted to operate with the new cutting assembly and the forming and applying assembly needs to be replaced with another forming and applying assembly having a diameter adapted to operate with the new spacer assembly.

Therefore, the format change involves the replacement of all the assemblies of the unit for feeding lateral flaps, and therefore becomes a very long and complex process; in this regard, it is important to note that the disassembly of the old assemblies and the subsequent mounting of the new assemblies of the unit for feeding lateral flaps, must comprise a setup step which is rather laborious and requires the involvement of an expert technician. Moreover, the replacement of the assemblies of the unit for feeding lateral flaps also requires a great deal in terms of costs, since for each format, assemblies of the unit for feeding lateral flaps must be provided, having a suitable size for the format and must be compatible with the assemblies with which it cooperates.

DESCRIPTION OF THE INVENTION

The object of the present invention is to provide a unit for feeding lateral flaps of a hygiene absorbent article and a method for the format change of the feeding unit, which feeding units and method for the format change do not have the drawbacks described above and, at the same time, are simple and inexpensive to produce.

According to the present invention a unit for feeding lateral flaps of a hygiene absorbent article and a method for the format change of the feeding unit are provided, as claimed in the attached claims.

BRIEF DESCRIPTION OF THE DRAWINGS

The present invention will now be described with reference to the accompanying drawings, which illustrate some examples of non-limiting embodiments, wherein.

PREFERRED EMBODIMENTS OF THE INVENTION

Figure 1:
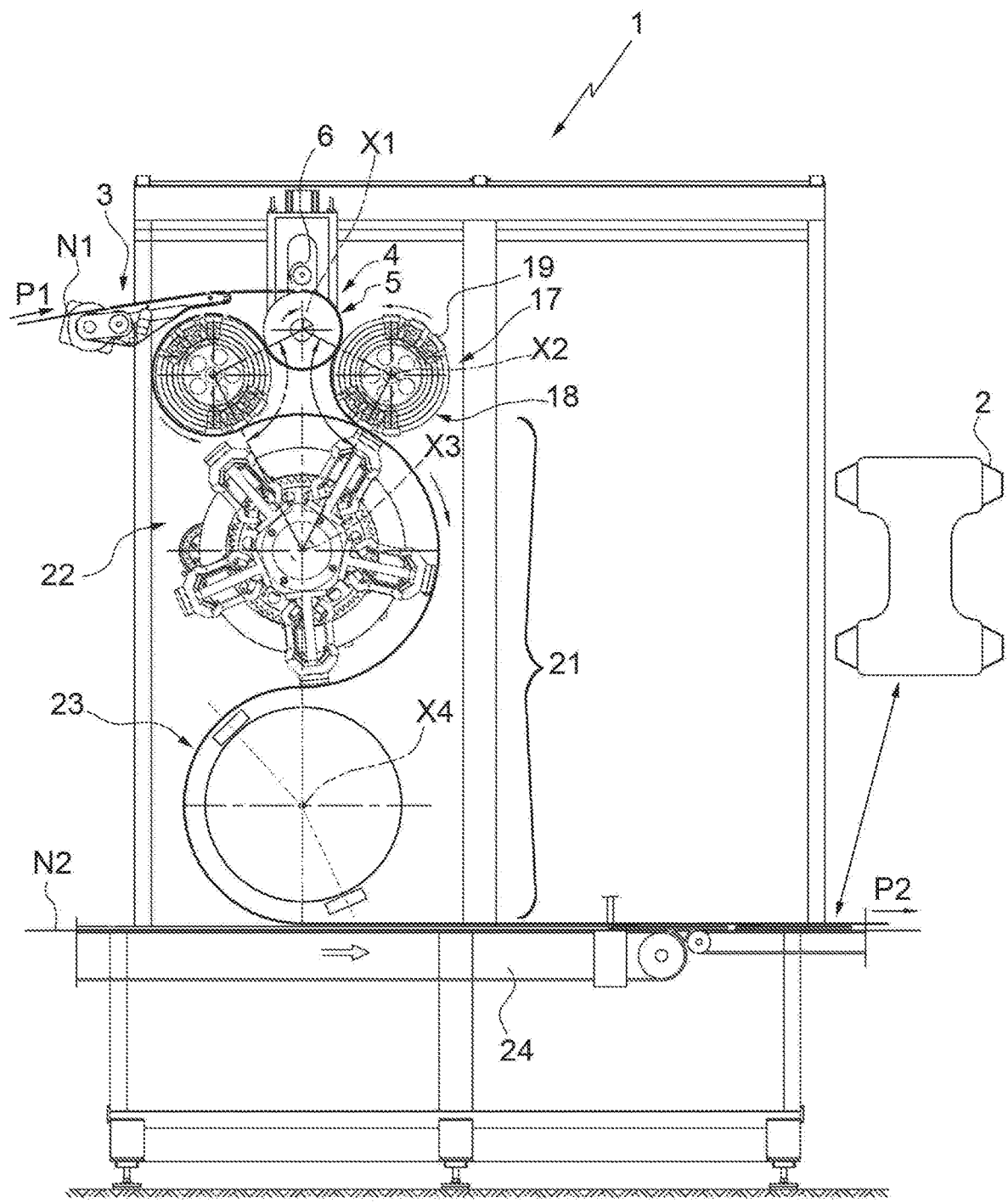
FIG. 1 is a schematic front view of the unit for feeding lateral flaps made according to the present invention.

In FIG. 1, number 1 denotes as a whole a unit for feeding lateral flaps 2 of a hygiene absorbent article. The feeding unit 1 comprises an input conveyor 3 which conveys along a feeding path P1 a continuous strip N1 from which the lateral flaps 2 are separated; the continuous strip N1 can be made of elastic material, or also of non-elastic material. The continuous strip N1 is then fed to a cutting assembly 4 in the area of which the single lateral flaps 2 are separated and appropriately shaped by means of corresponding transverse cuts.

The cutting assembly 4 is arranged downstream of the input conveyor 3 and comprises a receiving drum 5 mounted so as to rotate around a rotation axis X1 and a pair of blades 6 carried by a cutting drum which is arranged next to the receiving drum 5 and cooperates with the receiving drum 5 itself.

Figure 2:
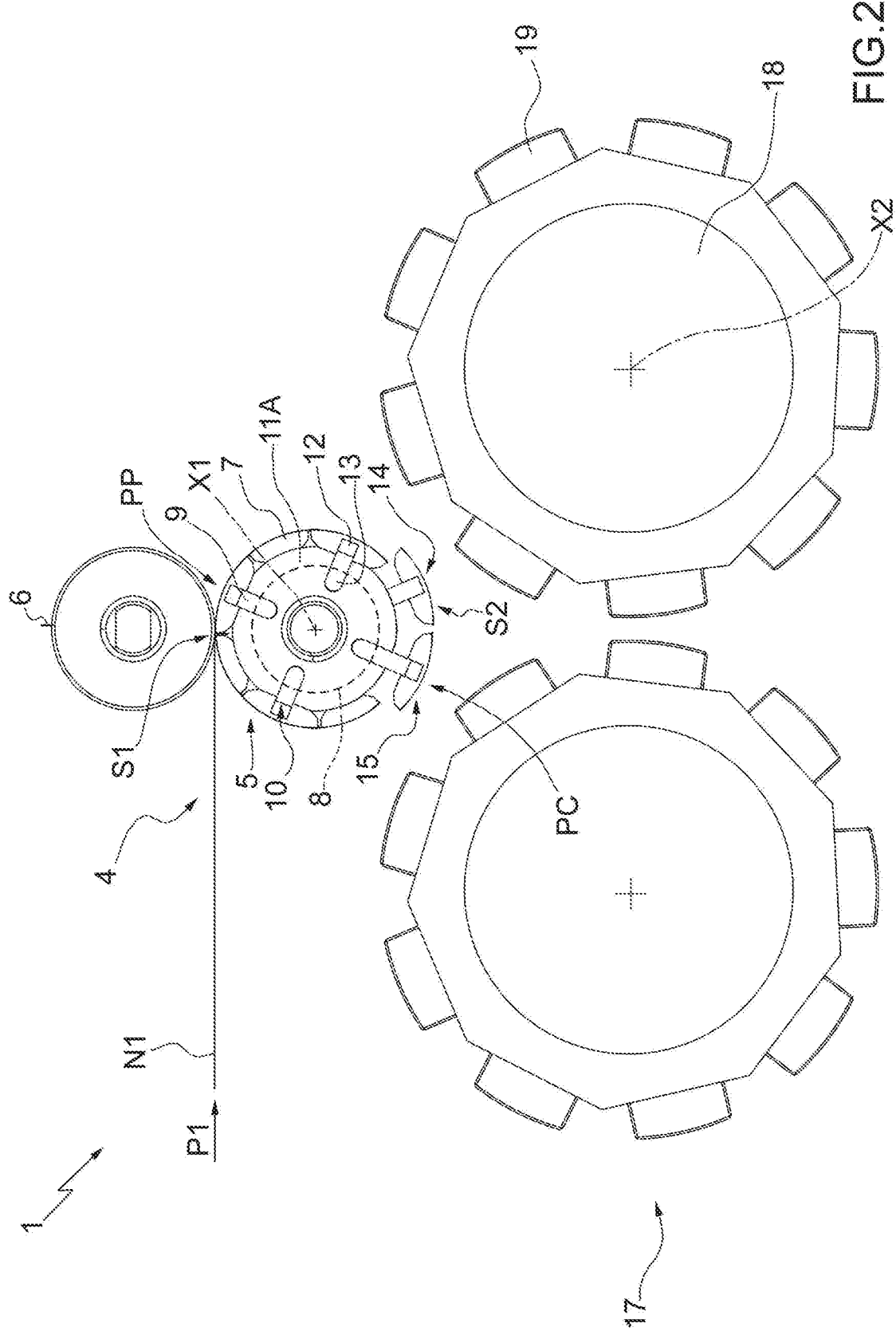
FIG. 2 is a schematic front view of a cutting assembly and of a spacer assembly of the feeding unit of FIG. 1.

Therefore, as illustrated in FIG. 2, the continuous strip N1 is fed to the receiving drum 5 in the area of an input station S1, thereafter it is cut into single lateral flaps 2 by means of the blades 6 which are arranged so as to cooperate with the receiving drum 5 and to cyclically cut the continuous strip N1 crosswise.

The receiving drum 5 is provided at the outer area thereof with a plurality of suction-pick up heads 7 which initially hold the continuous strip N1 until being cut and subsequently hold the single lateral flaps 2 separate from the continuous strip N1. In other words, the suction-pick up heads 7 are configured to hold the continuous strip N1 during cutting and subsequently hold the single lateral flaps 2 that have been cut.

As illustrated in FIG. 2, the suction-pick up heads 7 are mounted radially movable on the receiving drum 5. In particular, the suction-pick up heads 7 are radially moved relative to the receiving drum 5 by an actuator system 8. Therefore, the suction-pick up heads 7 are moved by the actuator system 8 that cyclically moves each suction-pick up head 7 radially between a radial pick-up position PP in the area of the input station S1 and a radial release position PC, which is different from the radial pick-up position PP, in the area of an output station S2.

According to a possible embodiment, the actuator system 8 comprises a cam system, i.e. the thrust for the radial movement of the suction-pick up heads 7 is generated by means of fixed cams arranged inside the receiving drum 5. According to an alternative embodiment, the actuator system 8 comprises electromechanical actuators (for example rotary electric motors or linear electric motors) which are mounted onto the receiving drum 5 and generate the thrust for the radial movement of the suction-pick up heads 7. The use of electromechanical actuators complicates the structure of the actuator system 8 and offers the advantage of being able to change the radial stroke of the suction-pick up heads 7 solely by acting on the control software (i.e. without any type of physical change to the actuator system 8).

Advantageously, in the radial pick-up position PP each suction-pick up head 7 is arranged closer to the rotation axis X1 relative to the release position PC. In other words, in the area of the radial pick-up position PP the suction-pick up head 7 has a smaller radial movement compared to the release position PC.

Advantageously, each suction-pick up head 7 is carried by a support arm 9 which is radially oriented and is arranged in the area of one end 10 of the suction-pick up head 7 in the area of a base wall 11A of the receiving drum 5. In particular, each support arm 9 has one outer end 12 integral with the corresponding suction-pick up head 7 and an inner end 13 which is mechanically connected to the actuator system 8.

Figure 3:
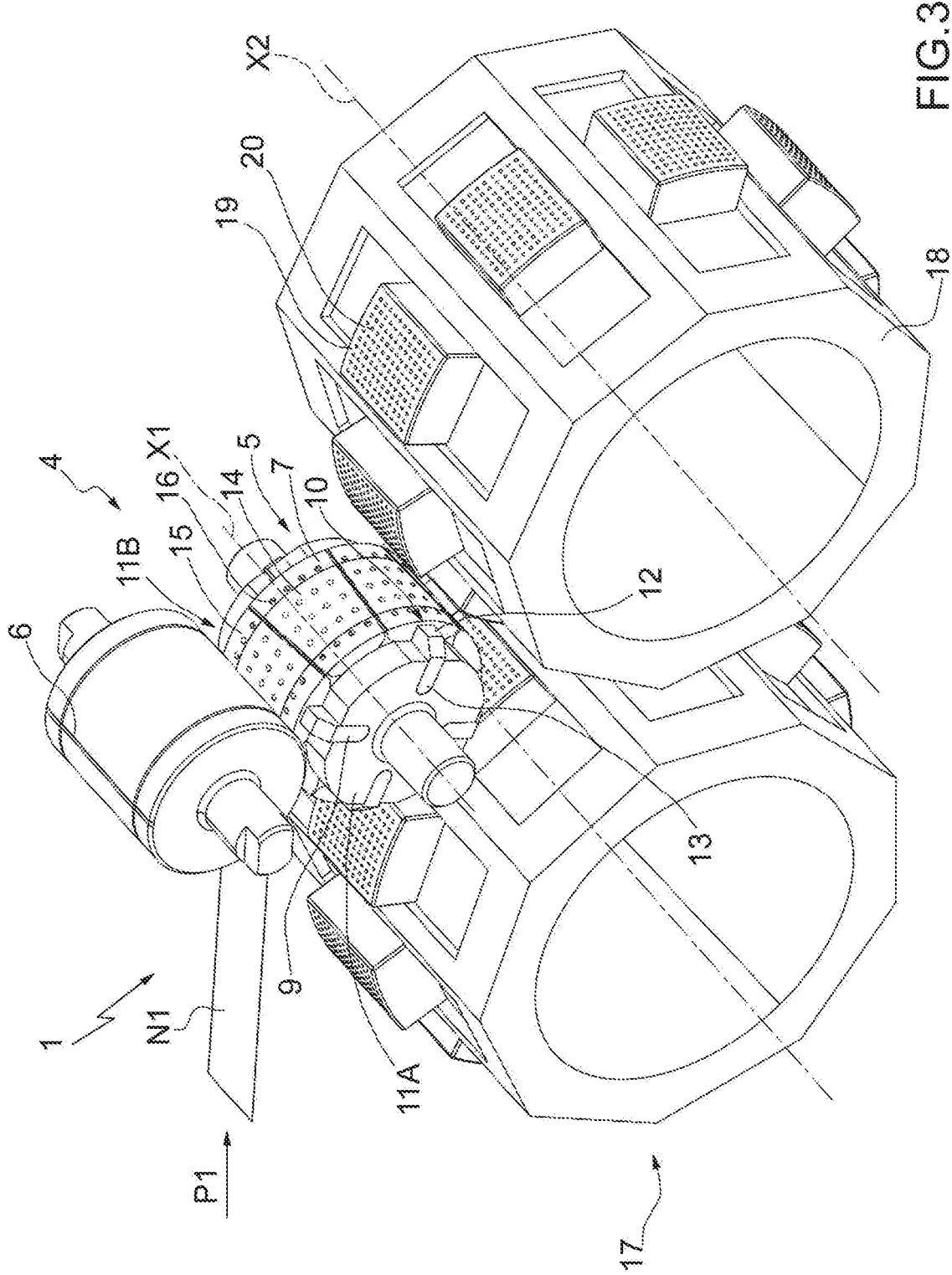
FIG. 3 is a perspective view of the cutting assembly and of the spacer assembly of FIG. 2.

In particular, as illustrated in FIGS. 2 and 3, the suction-pick up heads 7 are divided into two groups 14 and 15 based on the orientation of the conveyed lateral flap 2 (i.e. if the lateral flap 2 is right or left). In particular, the group 14 conveys only the lateral flaps 2 with a predetermined orientation (for example, all and only the right lateral flaps 2) and the group 15 conveys the lateral flaps 2 with an opposite orientation (for example, all and only the left lateral flaps 2). As clearly illustrated in FIG. 3, the suction-pick up heads 7 of the group 14 are alternated with the suction-pick up heads 7 of the group 15.

According to the preferred embodiment, all the support arms 9 for the suction-pick up heads 7 of the group 14 are arranged in the area of the base wall 11A of the receiving drum 5 and of all of the support arms 9 of the suction-pick up heads 7 of the second group 15 are arranged in the area of the base wall 11B of the receiving drum 5 which is opposite to the base wall 11A. In other words, the support arms 9 are alternately arranged in the area of the base wall 11A and of the base wall 11B of the receiving drum 5.

As illustrated in FIG. 3, the suction-pick up heads 7 have, in the area of the outer surface, suction holes 16 through which a vacuum is created to hold the continuous strip N1 (before being cut), or the cut lateral flaps 2 (after being cut).

As illustrated in FIG. 1, the lateral flaps 2, made by the cutting assembly 4, are thereafter fed to a spacer assembly 17 which is arranged downstream of the cutting assembly 4. The spacer assembly 17 comprises a pair of spacer drums 18, each of which is mounted so as to rotate around a rotation axis X2. The spacer drums 18 are arranged close to the receiving drum 5 and receive the lateral flaps 2 from the receiving drum 5 itself in its own output station S2, different from the output station S2 of the other spacer drum 18. In other words, the receiving drum 5 comprises two output stations S2 that are different one from the other and in the area in which the lateral flaps 2 are fed to each spacer drum 18.

Each spacer drum 18 is provided with a plurality of suction-pick up heads 19 which hold the single lateral flaps 2. Similarly, to the suction-pick up heads 7, the suction-pick up heads 19 have in the area of the outer surface suction holes 20 through which a vacuum is created to hold the cut lateral flaps 2. The suction-pick up heads 19 are made so as to be radially fixed and axially movable. In other words, while the suction-pick up heads 7 of the receiving drum 5 are made so as to be radially movable, the suction-pick up heads 19 of each spacer drum 18 are radially fixed (i.e. they do not move) and are instead axially movable.

As better illustrated in FIG. 2, the lateral flaps 2 coming from the cutting assembly 4 are alternately fed to each spacer drum 18 in two output stations S2. In other words, the suction-pick up heads 7 of the group 14 feed the lateral flaps only and exclusively to the spacer drum 18 dedicated thereto; similarly, the suction-pick up heads 7 of the group 15 feed the lateral flaps 2 only and exclusively to the spacer drum 18 dedicated thereto which is opposite to the spacer drum 18 dedicated to the group 14. In other words, each spacer drum 18 is configured to house and convey the lateral flaps 2 with a predetermined orientation (for example, all and only the right lateral flaps 2 or all and only the left lateral flaps 2).

Advantageously, the two spacer drums 18 are equal, so as to simplify the structure of the feeding unit 1.

As illustrated in FIG. 1, downstream of the spacer assembly 17 a forming and applying assembly 21 is arranged. The forming and applying assembly 21 comprises a forming drum 22 for the pairs of lateral flaps 2 which is mounted to rotate around a rotation axis X3, and an application drum 23 mounted in a rotatable manner around a rotation axis X4. In the area of the forming and applying assembly 21 two pairs of lateral flaps are formed, which are subsequently applied on a continuous strip N2 of absorbent material. The continuous strip N2 of absorbent material is conveyed by a main conveyor 24 along a feeding path P2 that passes through the feeding unit 1.

During a format change of the flaps 2 to be produced, it is necessary to replace the cutting assembly 4. Advantageously, the spacer assembly 17 and the forming and applying assembly 21 remain unchanged. In other words, during the format change of the lateral flaps 2 to be produced, the cutting assembly 4 must be only and exclusively replaced. In order to adapt to the new format, the new cutting assembly 4 comprises a receiving drum 5 having a diameter different compared to the receiving drum 5 of the previous cutting assembly 4; due to the difference in diameter of the new receiving drum 5, relative to the previous receiving drum 5, the new receiving drum 5 would not be able to cooperate with the spacer drums 18 of the spacer assembly 17. To compensate for the difference in diameter between the previous receiving drum 5 and the new receiving drum 5, relative to the diameter of the spacer drums (which does not change during the format change), the radial stroke of the suction-pick up heads 7 is adapted. In other words, the actuator system 8 radially moves each suction-pick up head 7 relative to the receiving drum 5 to bring the suction-pick up head 7 itself in contact with a corresponding second suction-pick up head 19 in the respective output station S2, as illustrated in FIG. 1 and in FIG. 3. For clarity, in FIG. 2 (which is a schematic view of the cutting assembly 4 and of the spacer assembly 17) the suction-pick up heads 7, which are located in the output station S2, have been illustrated spaced apart from the respective suction-pick up heads 19, even if in reality they are in contact.

Since the diameter of the new receiving drum 5 is different from the diameter of the previous receiving drum 5, an incompatibility between the new cutting assembly 4 and the spacer assembly 17 (with no changes in diameter of the spacer drums 18 during the format change) occurs, due to the change of the axle spacing between the receiving drum 5 and each of the spacer drums 18; to avoid this, as previously described, the suction-pick up heads 7 are mounted in a radially movable manner on the receiving drum 5 so as to be able to easily change their radial stroke. In other words, the suction-pick up heads 7, having been mounted as to be radially movable, allow to compensate for the change of the axle spacing by means of a corresponding change of the radial stroke of the suction-pick up heads 7 and thus ensuring the compatibility of the new cutting assembly 4 and the spacer assembly 17 (with no changes in diameter of the spacer drums 18 during the format change) arranged downstream.

In use, during the format change of the feeding unit 1 the previous cutting assembly 4 is replaced with a new cutting assembly 4, the same spacer drums 18 of the spacer assembly 17 are maintained and the stroke of the radial movement of the suction-pick up heads 7 between the radial pick-up position PP and the radial release position PC is changed. In other words, during the format change the previous cutting assembly 4 is replaced with a new cutting assembly 4, the same spacer assembly 17 and the same forming and applying assembly 21 are kept, and the stroke of the radial movement of the suction-pick up heads 7 between the radial pick-up position PP and the radial release position PC is changed. In this way, by way of the change in the stroke of the suction-pick up heads 7 a compensation for the difference in diameter between the receiving drum 5 of the previous cutting assembly 4 and the receiving drum 5 of the new cutting assembly 4 is provided. Moreover, in this way the suction-pick up heads 7 allow to change the pitch of the lateral flaps 2 between the input station S1 (in which the lateral flaps 2 have a smaller pitch) and the output station S2 (in which the lateral flaps 2 have a bigger pitch). In other words, by way of the radial movement of the suction-pick up heads 7 it is possible to obtain a pitch of the radial pick-up position PP (in the area of the input station S1) different from the pitch of the radial release position PC (in the area of the release station S2).

Therefore, in the area of the radial pick-up position PP, the suction-pick up heads 7 have a smaller pitch compared to the radial release position PC. In other words, the pitch in the area of the radial release position PC of the suction-pick up heads 7 is bigger than the pitch of the suction-pick up heads 7 themselves in the area of the radial pick-up position PP.

The feeding unit 1 described above has several advantages. Mainly, during the format change, the feeding unit 1 only requires the replacement of the cutting assembly 4. Therefore, the assemblies arranged downstream, that is, the spacer assembly 17 and the forming and applying assembly 21 are not replaced but only adapted. This allows to reduce the setup time induced by the new format and reduces the overall machine downtime.

In addition, the feeding unit 1 described above is also easy and inexpensive to produce, as the radial movement of the suction-pick up heads 7 is obtainable in a simple way by means of the use of a conventional type cam system 8.

The invention claimed is:
1. A unit (1) for feeding lateral flaps (2) of a hygiene absorbent article; the feeding unit (1) comprises:
an input conveyor (3) to convey a first continuous strip (N1) from which the lateral flaps (2) are separated;
a cutting assembly (4) arranged downstream of the input conveyor (3) and comprising: a receiving drum (5), which is mounted so as to rotate around a first rotation axis (X1), receives the first continuous strip (N1) in an input station (S1), and is provided with first suction-pick up heads (7), which are designed to hold the lateral flaps (2); and at least one blade (6), which cooperates with the receiving drum (5), to cyclically cut the first continuous strip (N1) crosswise, so as to separate the lateral flaps (2) from the first continuous strip (N1) itself; and
a spacer assembly (17), which is arranged downstream of the cutting assembly (4) and comprises a pair of spacer drums (18), each of which is mounted so as to rotate around a second rotation axis (X2), is provided with second suction-pick up heads (19) designed to hold the lateral flaps (2), and is arranged close to the receiving drum (5), to receive the lateral flaps (2) from the receiving drum (5); each spacer drum (18) receives the lateral flaps (2) from the receiving drum (5) at an output station (S2), wherein the receiving drum (5) includes two output stations (S2), a first output station (S2) for the first spacer drum (18) and a second output station (S2) for the second spacer drum (18); wherein the first output station (S2) is different than the second output station (S2);
wherein the receiving drum (5) alternatively feeds a lateral flap (2) to a spacer drum (18) and the following lateral flap (2) to the other spacer drum (18), so as to divide the lateral flaps (2) cut from the first continuous strip (N1) between the two spacer drums (18); the feeding unit (1) is characterized in that:
the first suction-pick up heads (7) are mounted to as to be radially movable on the receiving drum (5); and
an actuator system (8), which radially and cyclically moves each first suction-pick up head (7) between a radial pick-up position (PP) in the area of the input station (S1) and a radial release position (PC) is provided, which is different from the radial pick-up position (PP), in the area of the output station (S2).

2. The feeding unit according to claim 1, wherein the actuator system (8) radially moves each first suction-pick up head (7) relative to the receiving drum (5), so as to cause the first suction-pick up head (7) to come into contact with a corresponding second suction-pick up head (19) in the respective output station (S2).

3. The feeding unit according to claim 1, wherein, in the radial pick-up position (PP), each first suction-pick up head (7) is arranged closer to the first rotation axis (X1) compared to the release position (PC).

4. The feeding unit according to claim 1, wherein, in the area of the radial pick-up position (PP), the first suction-pick up heads (7) have a first pitch, whereas in the area of the radial release position (PC) the first suction-pick up head (7) have a second pitch, which is different from the first pitch.

5. The feeding unit according to claim 4, wherein the second pitch is greater than the first pitch.

6. The feeding unit according to claim 1, wherein:
the first suction-pick up heads (7) are divided into a first group (14), which exclusively releases the lateral flaps (2) to a spacer drum (18), and a second group (15), which exclusively releases the lateral flaps (2) to the other spacer drum (18); and the first suction-pick up heads (7) of the first group (14) are alternated with the first suction-pick up heads (7) of the second group (15).

7. The feeding unit according to claim 6, wherein each first suction-pick up head (7) is carried by a support arm (9), which is oriented radially and is arranged at an end (10) of the first suction-pick up head (7) in the area of a base wall (11A, 11B) of the receiving drum (5).

8. The feeding unit according to claim 7, wherein each support arm (9) has an outer end (12), which is integral with the corresponding first suction-pick up head (7), and an inner end (13), which is mechanically connected to the actuator system (8).

9. The feeding unit according to claim 8, wherein all the support arms (9) of the first suction-pick up heads (7) of the first group (14) are arranged in the area of a first base wall (11A) of the receiving drum (5) and all the support arms (9) of the first suction-pick up heads (7) of the second group (15) are arranged in the area of a second base wall (11B) of the receiving drum (5), which is opposite to the first base wall (11A).

10. The feeding unit according to claim 1 and comprising an assembly (21) for forming and applying the lateral flaps (2), which is arranged downstream of the spacer assembly (17), produces respective pairs of lateral flaps (2), and comprises a drum (22) for forming the pairs of lateral flaps (2), which is mounted so as to rotate around a third rotation axis (X3), and an applying drum (23), which is mounted so as to rotate around a fourth rotation axis (X4) and applies the pairs of lateral flaps (2) onto a second continuous strip (N2) of absorbent material.

11. A method for a format change of a feeding unit (1) according to claim 1; the format change method comprising:
replacing the previous cutting assembly (4) with a new cutting assembly (4), in which the receiving drum (5) has a diameter that is different from the diameter of the receiving drum (5) of the previous cutting assembly (4);
keeping the same spacer drums (18); and
changing the stroke of the radial movement of the first suction-pick up heads (7) between the pick-up position (PP) and the release position (PC).

12. The format change method according to claim 11, wherein the change of the stroke causes a compensation of the difference in diameter between the receiving drum (5) of the previous cutting assembly (4) and the receiving drum (5) of the new cutting assembly (4).

* * * * *